(12) United States Patent
Shimizu

(10) Patent No.: US 9,422,246 B2
(45) Date of Patent: Aug. 23, 2016

(54) BENZYLIDENE AZOLIDINE DERIVATIVE OR SALT THEREOF

(71) Applicant: ROHTO Pharmaceutical Co., Ltd., Osaka-shi (JP)

(72) Inventor: Takashi Shimizu, Osaka (JP)

(73) Assignee: ROHTO PHARMACEUTICAL CO., LTD., Osaka (JP)

(*) Notice: Subject to any disclaimer, the term of this patent is extended or adjusted under 35 U.S.C. 154(b) by 0 days.

(21) Appl. No.: 14/389,139

(22) PCT Filed: Mar. 27, 2013

(86) PCT No.: PCT/JP2013/059112
§ 371 (c)(1),
(2) Date: Sep. 29, 2014

(87) PCT Pub. No.: WO2013/146932
PCT Pub. Date: Oct. 3, 2013

(65) Prior Publication Data
US 2015/0065728 A1   Mar. 5, 2015

(30) Foreign Application Priority Data

Mar. 30, 2012 (JP) ................................. 2012-081037

(51) Int. Cl.
| C07D 233/96 | (2006.01) |
| A61Q 17/04 | (2006.01) |
| A61K 8/49 | (2006.01) |
| A61Q 19/00 | (2006.01) |

(52) U.S. Cl.
CPC .............. *C07D 233/96* (2013.01); *A61K 8/49* (2013.01); *A61K 8/494* (2013.01); *A61K 8/4946* (2013.01); *A61Q 17/04* (2013.01); *A61Q 19/00* (2013.01)

(58) Field of Classification Search
CPC ....... A61K 8/49; A61K 8/494; A61K 8/4946; A61Q 17/04; A61Q 19/00; C07D 233/96; C21B 13/004; C21B 13/0073; C21B 13/0086; C21B 13/14; C21B 2100/04
See application file for complete search history.

(56) References Cited

U.S. PATENT DOCUMENTS

| 2,719,141 | A | | 9/1955 | Smith | |
| 5,000,945 | A | * | 3/1991 | Kobayashi | ............... A61K 8/37 424/47 |
| 5,075,300 | A | | 12/1991 | Hindley et al. | |
| 5,087,729 | A | * | 2/1992 | Matsuno | .................. A61K 8/37 560/39 |

FOREIGN PATENT DOCUMENTS

| EP | 0632029 A1 | 1/1995 |
| JP | 02-083384 | 3/1990 |
| JP | 02-111760 A | 4/1990 |
| JP | H05-186430 | 7/1993 |
| JP | 06-082856 | 3/1994 |
| JP | H0682856 A | * 3/1994 |
| JP | 06306085 A | * 11/1994 |
| JP | H06-306085 | 11/1994 |
| JP | 07-070084 | 3/1995 |
| JP | 07-089838 | 4/1995 |
| JP | 3497246 B2 | 11/2003 |
| JP | 2011-526616 | 10/2011 |
| WO | WO 2010/001169 | 1/2010 |

OTHER PUBLICATIONS

Masaki et al. "Nonlinear Optical Material" JPH0682856A (Mar. 25, 1994) Machine Translation obtained on Sep. 30, 2015 from <http://worldwide.espacenet.com>.*
Mudit, et al. "Optimization of (Phenylmethylidene)-hydantoins as Prostate Cancer Migration Inhibitors: SAR-Directed Design, Synthesis, and Pharmacophore Modeling." Chemistry & Biodiversity 8.8 (2011): 1470-1485.
Popov-Pergal, et al. "Synthesis of 2-(5-arylidene-2,4-dioxotetrahydro-1,3-thiazolyl-3)-ethanols" J.Serb.Chem.Soc. 60(9)745-748(1995) (only pp. 745-747 are available).
Office Action issued in corresponding Taiwanese Patent Application No. 102111408, dated Apr. 10, 2015.
Office Action in Chinese Patent Application No. 201380017007.8, issued on Jun. 8, 2015.
Office Action in European Patent Application No. 13767915.5, dated Sep. 17, 2015.

* cited by examiner

*Primary Examiner* — Nyeemah A Grazier
*Assistant Examiner* — Amanda L Aguirre
(74) *Attorney, Agent, or Firm* — Knobbe, Martens, Olson & Bear, LLP

(57) ABSTRACT

A novel compound which has excellent ultraviolet-absorbing function (especially UVA absorbing function) and excellent hydrophilicity. A benzylidene azolidine derivative represented by structural formula (I) or a salt thereof. In structural formula (I), n represents an integer of 1-5; $A^1$ represents O, S or N-$A^4$; and each of $A^2$, $A^3$ and $A^4$ independently represents a hydrogen atom, an alkyl group which may be substituted by a hydroxyl group and has 1-8 carbon atoms, or the like (provided that at least one of $A^2$, $A^3$ and $A^4$ contains one or more hydroxyl groups). In this connection, when n is an integer of 2-5, the plurality of $A^3$O— moieties may be the same as or different.

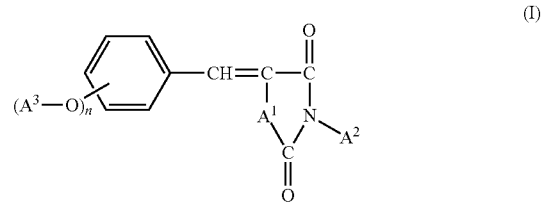

(I)

11 Claims, No Drawings

BENZYLIDENE AZOLIDINE DERIVATIVE OR SALT THEREOF

This application is the U.S. National Phase under 35 U.S.C. §371 of International Application No. PCT/JP2013/059112, filed Mar. 27, 2013, designating the U.S., and published in Japanese as WO 2013/146932 on Oct. 3, 2013, which claims priority to Japanese Patent Application No. 2012-081037 filed Mar. 30, 2012, the entire contents of which are incorporated herein by reference.

TECHNICAL FIELD

The invention relates to a novel benzylidene azolidine derivative or a salt thereof.

BACKGROUND ART

Ultraviolet rays are essential for the biosynthesis of vitamin D and also used to promote blood circulation or metabolism in the living body and to achieve sterilization or disinfection. On the other hand, excessive exposure of the skin to ultraviolet rays can cause skin cancer or promote skin aging which can cause freckles and wrinkles. Excessive exposure to ultraviolet rays can also cause the degradation of paints and a variety of synthetic resins such as polyethylene, polypropylene, PVC, and ABS resin. Thus, excessive exposure to ultraviolet rays can result in adverse effects.

To prevent such adverse effects, a variety of ultraviolet-absorbing agents have been developed and widely used.

Near ultraviolet rays usually called "ultraviolet rays (UV)" are broadly classified into UVA (315 to 400 nm in wavelength), UVB (280 to 315 nm in wavelength), and UVC (200 to 280 nm in wavelength). UVC, although derived from sunlight, is substantially absorbed by the ozone layer, etc., before reaching the earth, and thus usually does not reach the earth through the ozone layer, etc.

UVA and UVB are the main cause of skin cancer, skin aging, and the degradation of synthetic resins and paints.

Thus, ultraviolet-absorbing agents are developed for the purpose of absorbing mainly UVA or UVB.

Known examples of ultraviolet-absorbing materials contained in conventionally developed ultraviolet-absorbing agents include isooctyl p-methoxycinnamate, isoamyl p-methoxycinnamate, sodium phenylbenzimidazole sulfonate, 3-(4'-methylbenzylidene)-camphor, 4-tert-butyl-methoxy-dibenzoylmethane, and 4-isopropyl-dibenzoylmethane. These compounds all have an aromatic ring. The conjugated electrons in the aromatic ring can be excited with energy lower than that for non-conjugated electrons and thus can absorb ultraviolet rays. In addition, when the conjugated system is expanded, the electrons in the conjugated system can be excited with lower energy and thus can absorb long-wavelength ultraviolet rays and also visible rays.

Many UVB absorbing compounds suitable for practical use have been developed. Known examples of such UVB absorbing compounds include isooctyl p-methoxycinnamate, isoamyl p-methoxycinnamate, sodium phenylbenzimidazole sulfonate, and 3-(4'-methylbenzylidene)-camphor mentioned above.

On the other hand, many of conventional UVA absorbing compounds are decomposed in the process of converting the light energy of absorbed UVA into heat energy and releasing the heat energy. This means that such conventional UVA absorbing compounds have a problem with light stability, and at present, still few compounds have been developed to solve this problem.

Examples of currently developed UVA absorbing compounds include the hydantoin derivatives disclosed in Patent Documents 1 and 2.

When compositions for external use to skin, such as sunscreen compositions, are designed for use in water-contact activities such as sea bathing, they are required to have such properties that they can remain on skin parts where they are applied even when the skin parts comes into contact with water. Therefore, UVA absorbing compounds to be contained in such compositions should preferably have high oil solubility.

On the other hand, recently, as ultraviolet-induced skin damage and other complications have become well known, compositions for external use to skin such as sunscreen compositions have come to be used also in daily life (in other words, in situations where skin parts to which they are applied do not necessarily come into contact with water). For such applications, UVA absorbing compounds contained in compositions are required to have high hydrophilicity so that the compositions can be free of sticky feeling, crustiness, or white residue during use and also can be easily washed off from skin parts after use (good removability).

The hydantoin derivatives disclosed in Patent Documents 1 and 2 are too low in hydrophilicity to be used in such compositions for external use to skin. Compositions for external use to skin containing such derivatives can hardly fulfill these functions at the same time.

Thus, conventional azolidine derivatives have room for improvement because they cannot exhibit good hydrophilicity simultaneously with high ability to absorb ultraviolet rays (particularly UVA).

PRIOR ART DOCUMENTS

Patent Documents

Patent Document 1: JP-A-02-111760
Patent Document 2: Japanese Patent No. 3497246

SUMMARY OF THE INVENTION

Problems to be Solved by the Invention

It is an object of the invention to provide a novel compound having a high level of hydrophilicity and ultraviolet-absorbing properties (particularly UVA absorbing properties).

Means for Solving the Problems

As a result of earnest study, the inventor has accomplished the invention based on findings that when existing benzylidene azolidine derivatives are modified with specific functional groups, they can have not only good ultraviolet-absorbing properties (particularly good UVA absorbing properties) but also good hydrophilicity.

Specifically, the invention has the following features.

The invention is directed to a benzylidene azolidine derivative represented by structural formula (I):

[Formula 1]

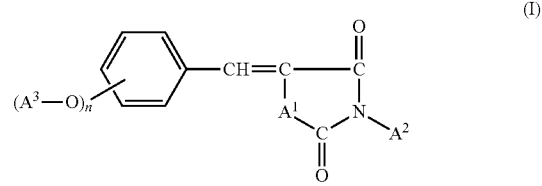

wherein n is an integer of 1 to 5, $A^1$ is O, S, or N-$A^4$, $A^2$, $A^3$, and $A^4$ are each independently a hydrogen atom, an optionally hydroxyl-substituted alkyl group of 1 to 8 carbon atoms, a functional group (1) represented by structural formula (1):

[Formula 2]

(1)

wherein $X^1$ is an alkylene group of 2 to 4 carbon atoms, $R^1$ is a hydroxyalkyl group of 2 to 4 carbon atoms, and m is an integer of 1 to 4, provided that when m is an integer of 2 to 4, two or more occurrences of $X^1$ may be the same or different, a functional group (2) represented by structural formula (2):

[Formula 3]

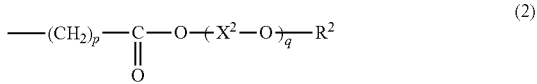

(2)

wherein $X^2$ is an alkylene group of 2 to 4 carbon atoms, $R^2$ is a hydroxyalkyl group of 2 to 4 carbon atoms, p is 1 or 2, and q is an integer of 0 to 4, provided that when q is an integer of 2 to 4, two or more occurrences of $X^2$ may be the same or different, or a functional group (3) represented by structural formula (3):

[Formula 4]

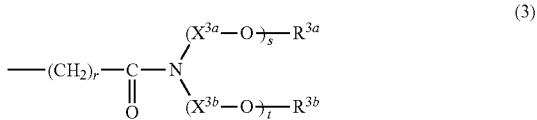

(3)

wherein $X^{3a}$ and $X^{3b}$ are each independently a hydrogen atom or an alkylene group of 2 to 4 carbon atoms, $R^{3a}$ and $R^{3b}$ are each independently a hydroxyalkyl group of 2 to 4 carbon atoms, r is 1 or 2, s and t are each independently an integer of 0 to 4, provided that when s is an integer of 2 to 4, two or more occurrences of $X^{3a}$ may be the same or different and when t is an integer of 2 to 4, two or more occurrences of $X^{3b}$ may be the same or different, provided that at least one of $A^2$, $A^3$, and $A^4$ has at least one hydroxyl group and provided that when n is an integer of 2 to 5, two or more occurrences of $A^3O$— may be the same or different, or a salt thereof.

In the benzylidene azolidine derivative or salt thereof according to the invention, at least one of $A^2$, $A^3$, and $A^4$ in structural formula (I) is preferably the functional group (1), (2), or (3).

In the benzylidene azolidine derivative or salt thereof according to the invention, $A^2$ and/or $A^3$ in structural formula (I) is preferably a hydrogen atom, a hydroxyl-substituted alkyl group of 1 to 8 carbon atoms, or the functional group (1), (2), or (3).

The benzylidene azolidine derivative or salt thereof according to the invention is preferably a benzylidene hydantoin derivative represented by structural formula (II):

[Formula 5]

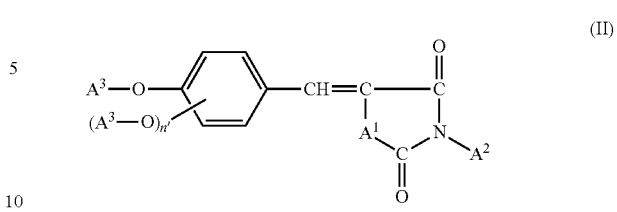

(II)

wherein n' is an integer of 0 to 4, provided that when n' is an integer of 1 to 4, two or more occurrences of $A^3$-O— may be the same or different, or a salt thereof.

The benzylidene azolidine derivative or salt thereof according to the invention is preferably a benzylidene hydantoin derivative represented by structural formula (III):

[Formula 6]

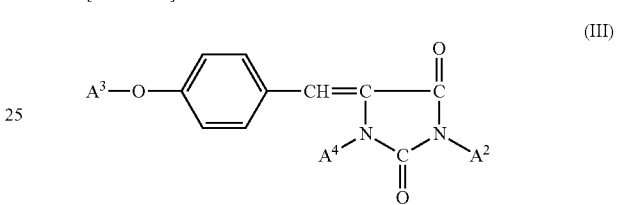

(III)

or a salt thereof.

The invention is also directed to an ultraviolet-absorbing agent including the benzylidene azolidine derivative or salt thereof according to the invention.

The invention is also directed to an composition for external use to skin, including the benzylidene azolidine derivative or salt thereof according to the invention.

Effect of the Invention

The benzylidene azolidine derivative or salt thereof according to the invention can have not only good ultraviolet-absorbing properties (particularly good UVA absorbing properties) but also good hydrophilicity.

MODE FOR CARRYING OUT THE INVENTION

Hereinafter, the benzylidene azolidine derivative and the salt thereof according to the invention, the ultraviolet-absorbing agent according to the invention, and the composition for external use to skin according to the invention will be described.

[Benzylidene Azolidine Derivative and Salt Thereof]

The benzylidene azolidine derivative according to the invention is represented by structural formula (I) below.

[Formula 7]

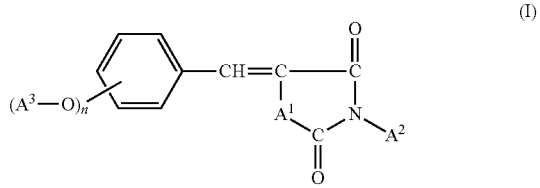

(I)

In structural formula (I), the moieties represented by structural formulae (i) and (ii) below are referred to as the "benzene ring moiety (i)" and the "azolidine moiety (ii)," respectively.

[Formula 8]

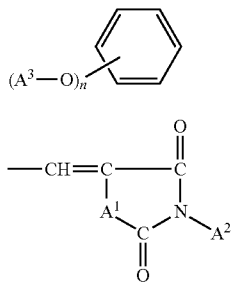

As shown in structural formula (I), the azolidine moiety (ii) contains the N-$A^2$ moiety. When $A^1$ is N-$A^4$, the azolidine moiety (ii) also contains the N-$A^4$ moiety. The nitrogen atom in each of the N-$A^2$ and N-$A^4$ moieties is basic. Therefore, an inorganic or organic acid can be added to the N atom to form an acid addition salt. Examples of such an inorganic acid include hydrochloric acid, sulfuric acid, nitric acid, phosphoric acid, and hydrobromic acid. Examples of such an organic acid include acetic acid, citric acid, gluconic acid, tartaric acid, fumaric acid, maleic acid, lactic acid, methanesulfonic acid, and p-toluenesulfonic acid.

As compared with the benzylidene azolidine derivative according to the invention, the salt of the benzylidene azolidine derivative according to the invention is advantageous in that it can have higher hydrophilicity or easily become a solid so that it can be easily handled.

In structural formula (I) and the other structural formulae shown in the description, n, $A^1$, $A^2$, and $A^3$ are defined as follows.

(1) n

The letter n is an integer of 1 to 5. To exhibit higher specific absorbance (ultraviolet absorbance per mass) and higher UV absorbing properties, n is preferably an integer of 1 to 3, more preferably 1.

(2) $A^1$ $A^1$ is O, S, or N-$A^4$. For the ability to effectively absorb UVA and light in a wavelength range close to that of UVA, $A^1$ is preferably N-$A^4$.

(3) $A^2$, $A^3$, and $A^4$ $A^2$, $A^3$, and $A^4$ are each independently a hydrogen atom, an optionally hydroxyl-substituted alkyl group of 1 to 8 carbon atoms, a functional group represented by structural formula (1) below (functional group (1)), a functional group represented by structural formula (2) below (functional group (2)), or a functional group represented by structural formula (3) below (functional group (3)).

To improve UV absorbing properties, at least one of $A^2$, $A^3$, and $A^4$ is preferably the functional group (1), (2), or (3), and at least two of $A^2$, $A^3$, and $A^4$ are preferably the functional group (1), (2), or (3).

[Formula 9]

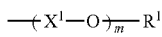 (2)

In structural formula (1), $X^1$ is an alkylene group of 2 to 4 carbon atoms, $R^1$ is a hydroxyalkyl group of 2 to 4 carbon atoms, and m is an integer of 1 to 4, provided that when m is an integer of 2 to 4, two or more occurrences of $X^1$ may be the same or different.

[Formula 10]

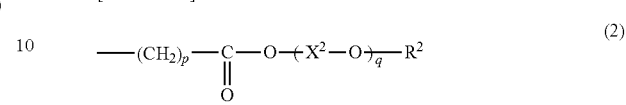

In structural formula (2), $X^2$ is an alkylene group of 2 to 4 carbon atoms, $R^2$ is a hydroxyalkyl group of 2 to 4 carbon atoms, p is 1 or 2, and q is an integer of 0 to 4, provided that when q is an integer of 2 to 4, two or more occurrences of $X^2$ may be the same or different.

[Formula 11]

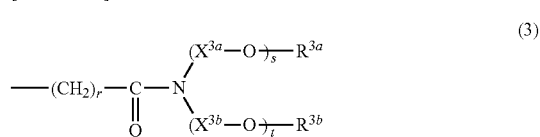

In structural formula (3), $X^{3a}$ and $X^{3b}$ are each independently a hydrogen atom or an alkylene group of 2 to 4 carbon atoms, $R^{3a}$ and $R^{3b}$ are each independently a hydroxyalkyl group of 2 to 4 carbon atoms, r is 1 or 2, s and t are each independently an integer of 0 to 4, provided that when s is an integer of 2 to 4, two or more occurrences of $X^{3a}$ may be the same or different and when t is an integer of 2 to 4, two or more occurrences of $X^{3b}$ may be the same or different.

When n is an integer of 2 to 5, two or more occurrences of $A^3$O— may be the same or different.

For the ability to exhibit high water solubility, at least one of $A^1$, $A^2$, and $A^3$-O— is preferably a hydroxyl group-containing functional group.

(3-1) Optionally Hydroxyl-Substituted Alkyl Group of 1 to 8 Carbon Atoms

The optionally hydroxyl-substituted alkyl group of 1 to 8 carbon atoms may be any linear or branched alkyl group having 1 to 8 carbon atoms, which may be substituted with a hydroxyl group (to form a hydroxyalkyl group) or unsubstituted with a hydroxyl group. To improve UV absorbing properties and water solubility or hydrophilicity, a linear or branched hydroxyalkyl group of 1 to 8 carbon atoms is particularly preferred.

For the ability to exhibit higher specific absorbance (ultraviolet absorbance per mass), the alkyl group preferably has 1 to 8 carbon atoms, more preferably 1 to 4 carbon atoms.

(3-2) Functional Group (1)

The functional group (1) has structural formula (1) above. In the formula, $X^1$ is an alkylene group of 2 to 4 carbon atoms. The alkylene group may be linear or branched. For the ability to exhibit higher specific absorbance (ultraviolet absorbance per mass), the alkylene group for $X^1$ preferably has 1 to 2 carbon atoms (for example, the alkylene group is preferably a methylene group (—$CH_2$—) or an ethylene group (—$CH_2CH_2$—).

$R^1$ is a hydroxyalkyl group of 2 to 4 carbon atoms (or an alkyl group of 2 to 4 carbon atoms substituted with at least one hydroxyl group). For the ability to exhibit higher specific absorbance (ultraviolet absorbance per mass) and the ability to be produced from general-purpose reagent raw materials, $R^1$ is preferably a hydroxyalkyl group of 2 carbon atoms, more preferably a hydroxyethyl group ($-CH_2CH_2OH$).

The letter m is an integer of 1 to 4. For the ability to exhibit higher specific absorbance (ultraviolet absorbance per mass) and the ability to be produced from general-purpose reagent raw materials, m is preferably an integer of 1 to 2, more preferably 1.

When m is an integer of 2 to 4, two or more occurrences of $X^1$ may be the same or different. In this case, for the ability to exhibit higher specific absorbance (ultraviolet absorbance per mass) and the ability to be produced from general-purpose reagent raw materials, two or more $X^1$ groups are preferably methylene groups ($-CH_2-$) or ethylene groups ($-CH_2CH_2-$).

(3-3) Functional Group (2)

The functional group (2) has structural formula (2) above. In the formula, $X^2$ is an alkylene group of 2 to 4 carbon atoms. The alkylene group may be linear or branched. For the ability to exhibit higher specific absorbance (ultraviolet absorbance per mass) and the ability to be produced from general-purpose reagent raw materials, the alkylene group for $X^2$ preferably has 1 to 2 carbon atoms (for example, the alkylene group is preferably a methylene group ($-CH_2-$) or an ethylene group ($-CH_2CH_2-$).

$R^2$ is a hydroxyalkyl group of 2 to 4 carbon atoms (or an alkyl group of 2 to 4 carbon atoms substituted with at least one hydroxyl group). For the ability to exhibit higher specific absorbance (ultraviolet absorbance per mass) and the ability to be produced from general-purpose reagent raw materials, $R^2$ is preferably a hydroxyalkyl group of 2 carbon atoms, more preferably a hydroxyethyl group ($-CH_2CH_2OH$).

The letter p is 1 or 2. For the ability to exhibit higher specific absorbance (ultraviolet absorbance per mass), p is preferably 1.

The letter q is an integer of 0 to 4. For the ability to exhibit higher specific absorbance (ultraviolet absorbance per mass) and the ability to be produced from general-purpose reagent raw materials, q is preferably an integer of 1 to 2, more preferably 1.

When q is an integer of 2 to 4, two or more occurrences of $X^1$ may be the same or different. In this case, for the ability to exhibit higher specific absorbance (ultraviolet absorbance per mass) and the ability to be produced from general-purpose reagent raw materials, two or more $X^1$ groups are preferably methylene groups ($-CH_2-$) or ethylene groups ($-CH_2CH_2-$).

(3-4) Functional Group (3)

The functional group (3) has structural formula (3) above. In the formula, $X^{3a}$ and $X^{3b}$ are each independently an alkylene group of 2 to 4 carbon atoms. The alkylene group may be linear or branched. For the ability to exhibit higher specific absorbance (ultraviolet absorbance per mass), $X^{3a}$ and $X^{3b}$ are preferably each independently an alkylene group of 2 to 4 carbon atoms (for example, the alkylene group is preferably a methylene group ($-CH_2-$) or an ethylene group ($-CH_2CH_2-$)).

$R^{3a}$ and $R^{3b}$ are each independently a hydroxyalkyl group of 2 to 4 carbon atoms (or an alkyl group of 2 to 4 carbon atoms substituted with at least one hydroxyl group). For the ability to exhibit higher specific absorbance (ultraviolet absorbance per mass) and the ability to be produced from general-purpose reagent raw materials, $R^{3a}$ and $R^{2b}$ are preferably hydroxyalkyl groups of 2 carbon atoms, more preferably hydroxyethyl groups ($-CH_2CH_2OH$).

The letter r is 1 or 2. For the ability to exhibit higher specific absorbance (ultraviolet absorbance per mass), r is preferably 1.

The letters s and t are each independently an integer of 0 to 4. For the ability to exhibit higher specific absorbance (ultraviolet absorbance per mass) and the ability to be produced from general-purpose reagent raw materials, s and t are each preferably an integer of 1 to 2, more preferably 1.

When s is an integer of 2 to 4, two or more occurrences of $X^{3a}$ may be the same or different. When t is an integer of 2 to 4, two or more occurrences of $X^{3b}$ may be the same or different. In this case, for the ability to exhibit higher specific absorbance (ultraviolet absorbance per mass) and the ability to be produced from general-purpose reagent raw materials, two or more $X^{3a}$ groups are preferably methylene groups ($-CH_2-$) or ethylene groups ($-CH_2CH_2-$), and two or more $X^{3b}$ groups are preferably methylene groups ($-CH_2-$) or ethylene groups ($-CH_2CH_2-$).

(3-5) $A^2$

To further improve hydrophilicity, $A^2$ is preferably a hydrogen atom, a hydroxyalkyl group of 1 to 8 carbon atoms, which has a hydroxyl group as a substituent, or the functional group (1), (2), or (3), more preferably a hydroxyalkyl group of 1 to 8 carbon atoms, which has a hydroxyl group as a substituent, or the functional group (1), (2), or (3), even more preferably the functional group (1) or (3).

(3-6) $A^3$

As stated above, $A^3$ is a hydrogen atom, an optionally hydroxyl-substituted alkyl group of 1 to 8 carbon atoms, or any one of the functional groups (1) to (3). Therefore, the $A^3$-O— moiety bonded to the benzene ring moiety (i) is an electron-donating group. When the benzylidene azolidine derivative of structural formula (I) or the salt thereof according to the invention is irradiated with UV, a resonance effect occurs so that electrons are donated from the $A^3$-O— group to the benzene ring, which allows effective expansion of the benzene ring conjugated system. Thus, the benzylidene azolidine derivative or the salt thereof according to the invention has high UV absorbing properties to absorb long-wavelength ultraviolet rays (e.g., UVA).

To further improve UV absorbing properties, $A^3$ is preferably a hydrogen atom, a hydroxyalkyl group of 1 to 8 carbon atoms, or the functional group (1), (2), or (3), more preferably the functional group (1) or (3).

To further improve UV absorbing properties, the $A^3$-O— group is preferably bonded to the para position of the benzene ring moiety (i) with respect to the azolidine moiety (ii). Such a benzylidene azolidine derivative may be represented by structural formula (II) below.

[Formula 12]

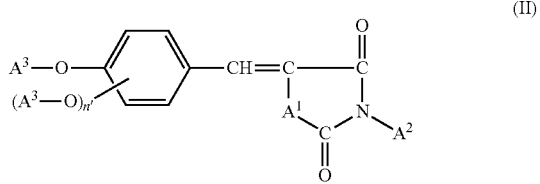

(II)

In structural formula (II), n' is an integer of 0 to 4, provided that when n' is an integer of 1 to 4, two or more occurrences of $A^3$-O— may be the same or different, $A^3$ is a hydrogen atom, a hydroxyl-substituted alkyl group of 1 to 8 carbon atoms, or the functional group (1), (2), or (3).

To further improve UV absorbing properties and hydrophilicity, n' is preferably 0 and $A^1$ is preferably $N-A^4$ in structural formula (II). Therefore, the benzylidene azolidine derivative according to the invention is preferably represented by structural formula (III) below.

[Formula 13]

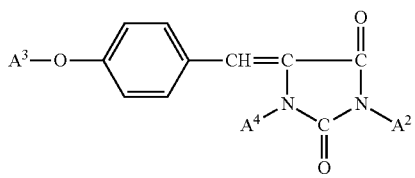

(III)

In view of easiness of synthesis (or to shorten the synthetic pathway), $A^2$ and $A^3$ are more preferably the same functional group.

(3-7) $A^4$

To further improve UV absorbing properties and hydrophilicity, $A^4$ is preferably a hydrogen atom or the functional group (3), more preferably a hydrogen atom.

(4) Molecular Weight

For the ability to exhibit a high level of absorbance and safety in a well-balanced manner, the benzylidene hydantoin derivative according to the invention generally has a molecular weight of 250 to 1,000, preferably 300 to 500. The molecular weight is preferably 300 or more so that the risk of an adverse effect such as stimulation or toxicity caused by transdermal absorption into the body can be reduced.

[Ultraviolet-Absorbing Agent]

The ultraviolet-absorbing agent according to the invention contains, as an essential component, the benzylidene azolidine derivative or the salt thereof according to the invention. Therefore, the ultraviolet-absorbing agent according to the invention has a high ability to absorb ultraviolet rays and a high level of light stability and hydrophilicity. In particular, therefore, the ultraviolet-absorbing agent according to the invention is advantageously used to form an aqueous composition (an aqueous solution or emulsion). It will be understood that if necessary, the ultraviolet-absorbing agent according to the invention may also contain an optional component as described below in addition to the benzylidene azolidine derivative or the salt thereof.

Examples of the optional component include a known organic ultraviolet-absorbing agent (a) other than the benzylidene azolidine derivative or the salt thereof and a powdery inorganic ultraviolet blocking agent (b).

Examples of the organic ultraviolet-absorbing agent (a) include benzoic acid derivatives such as isooctyl p-dimethylaminobenzoate, camphor derivatives such as 3-(4'-methylbenzylidene)-camphor, cinnamic acid derivatives such as isooctyl p-methoxycinnamate, benzophenone derivatives such as 2-hydroxy-4-methoxybenzophenone, dibenzoylmethane derivatives such as 4-tert-butyl-methoxy-dibenzoylmethane, salicylic acid derivatives such as octyl salicylate, benzimidazole derivatives such as sodium phenylbenzimidazole sulfonate, triazole derivatives such as 2,2'-methylenebis(6-(2H-benzotriazol-2-yl)-4-(1,1,3,3-tetra methylbutyl)phenol, and triazine derivatives such as 2,4,6-tris[4-(2-ethylhexyloxycarbonyl)anilino]-1,3,5-triazine.

Examples of the powdery inorganic ultraviolet blocking agent (b) include zinc oxide, zirconium oxide, cerium oxide, or titanium oxide.

[Composition for External Use to Skin]

The composition for external use to skin according to the invention contains, as an essential component, the benzylidene azolidine derivative or the salt thereof according to the invention described above. The composition for external use to skin may be a cosmetic composition, a sunscreen composition, or the like. In particular, the composition is preferably an aqueous composition for external use to skin (an aqueous solution or emulsion composition for external use to skin).

The composition for external use to skin according to the invention, which contains, as an essential component, the benzylidene azolidine derivative or the salt thereof according to the invention, has high ultraviolet-absorbing properties. Therefore, the composition according to the invention can reduce damage caused by exposure to UV at hair and skin parts of the human or animal body, to which the composition is applied. In addition, the benzylidene azolidine derivative or the salt thereof in the composition for external use to skin (particularly, the aqueous composition for external use to skin) according to the invention has high hydrophilicity. Therefore, after applied to parts of the body, the composition for external use to skin according to the invention has high removability so that the benzylidene azolidine derivative or the salt thereof can be easily removed by washing the parts with water without using any special cleaner.

As used herein, the term "aqueous composition for external use to skin" refers to a composition for external use to skin, such as a lotion, typically containing 30 to 99% by weight of water based on 100% by weight of the composition.

The benzylidene azolidine derivative or the salt according to the invention may be substantially free of an acidic group such as a sulfonic acid group or a basic group. In this case, the benzylidene azolidine derivative or the salt thereof has no significant effect on the pH of the composition for external use to skin, and therefore, the composition for external use to skin according to the invention may contain substantially any known components.

Thus, the composition for external use to skin according to the invention may be used in the form of a sunscreen composition or any other form that is suitable for everyday use and meets current needs such as good removability.

The composition for external use to skin according to the invention may contain, for example, the organic ultraviolet-absorbing agent (a), the powdery inorganic ultraviolet blocking agent (b), liquid oils and fats, solid oils and fats, wax, hydrocarbons, higher fatty acids, higher alcohols, esters, silicones, anionic surfactants, cationic surfactants, amphoteric surfactants, nonionic surfactants, moisturizing agents, water-soluble polymers, thickeners, coating materials, sequestering agents, lower alcohols, polyhydric alcohols, saccharides, amino acids, organic amines, pH adjusting agents, skin nutrients, vitamins, antioxidants, perfume and flavor materials, powders, colorants, water, or other materials.

[Paints and Other Materials]

The benzylidene hydantoin derivative or the salt thereof according to the invention may also be added to materials other than composition for external use to skin, such as paint compositions, dyes, pigments, a variety of resins, synthetic rubber, latex, packaging materials (such as films or synthetic resin containers), contact lenses, or fibers to form a variety of compositions or products, which are protected from ultraviolet rays.

The paint compositions generally contain a colorant such as a pigment or a dye, a vehicle including a solution of synthetic resin in a solvent, and an assistant (such as a drying regulator or a coating regulator). Examples of the synthetic resin include vinyl chloride resin, chlorinated polypropylene, vinyl chloride-vinyl acetate copolymers, nitrocellulose, polyurethane, polyester, polyamide, organosiloxane polymers, acrylic resin, aminoalkyd resin, epoxy resin, silica resin, fluororesin-containing polycarbonate resin, melamine resin, diethylene glycol bisallyl carbonate resin, polyethylene resin, and polystyrene resin.

The paint compositions may also contain an additive such as an oligomer (a prepolymer or a photo-polymerizable oligomer), a monomer (a reactive diluent or a photo-polymerizable monomer), a photopolymerization initiator (sensitizer), a light stabilizer, an antifoaming agent, a pigment dispersant, a leveling agent, an anti-sagging agent, a delustering agent, an antioxidant, a heat resistance improver, a slip agent, a preservative, or a fluorescent brightening agent.

The dyes may be any of various conventionally known dyes. The dyes may also be mixed with an additive such as the organic ultraviolet-absorbing agent (a), the powdery inorganic ultraviolet blocking agent (b), an alkali such as sodium carbonate, sodium silicate, or sodium hydroxide, water, an organic solvent, a surfactant, a pH adjusting agent, a preservative, or a dispersing agent.

The pigments may be any of various conventionally known pigments. The pigments may also be mixed with an additive such as water, an organic solvent, a pH adjusting agent, water-soluble resin, a resin emulsion, a preservative, or a pigment dispersant.

The variety of resins may be, for example, polyethylene resins, polypropylene resins, vinyl chloride resins, styrene resins, acrylic resins, polyurethane, polyester, polyamide, polyimide, polyphenylene ether, polysulfone, polyether sulfone, polyether ether ketone, polyacetal, organosiloxane polymers, aminoalkyd resins, epoxy resins, fluororesins, silicone resins, melamine resins, diethylene glycol bisallyl carbonate resins, ethylene-(meth)acrylic acid copolymers or ionomers thereof, polyvinyl alcohol, polyether imide, ethylene-vinyl acetate copolymers, ethylene-vinyl alcohol copolymers, polyphenylene sulfide, polycarbonate, cellulose, nitrocellulose, and ABS resins.

These resins may also be modified with polymerizable compounds having any of various functional groups, such as maleic acid, by graft polymerization.

These various resins may also be mixed with an additive such as the organic ultraviolet-absorbing agent (a), the powdery inorganic ultraviolet blocking agent (b), a solvent, a light stabilizer, an antioxidant, a colorant, a light diffusing agent, aflame retardant, an anti-discoloration agent, an antistatic agent, a plasticizer, a filler, a pigment, or inorganic fine particles.

Examples of the synthetic rubber include acrylic rubber, nitrile rubber, isoprene rubber, urethane rubber, ethylene propylene rubber, epichlorohydrin rubber, chloroprene rubber, silicone rubber, styrene-butadiene rubber, butadiene rubber, fluororubber, and polyisobutylene rubber.

The synthetic rubber may also be mixed with an additive such as the organic ultraviolet-absorbing agent (a), the powdery inorganic ultraviolet blocking agent (b), a solvent, a light stabilizer, an antioxidant, a colorant, a light diffusing agent, a flame retardant, an anti-discoloration agent, an antistatic agent, a plasticizer, a filler, a pigment, or inorganic fine particles.

The resin material used to form the latex may be any of those capable of forming a latex among the variety of resins. The latex may also be mixed with an additive such as the organic ultraviolet-absorbing agent (a), the powdery inorganic ultraviolet blocking agent (b), a surfactant, a pH adjusting agent, a filler, a complexing agent, an antioxidant, a dye, a pigment, a plasticizer, a vulcanizing agent, a vulcanizing accelerator, a biocidal agent, a fungicide, or an antifoaming agent.

Examples of the material used to form the film include polyethylene resin, polypropylene resin, vinyl chloride resin, styrene resin, polyester, polyamide, polyurethane, polyimide, polycarbonate, ethylene-vinyl alcohol copolymers, polyvinyl alcohol films, ethylene-vinyl acetate copolymers, acrylic resin, and ABS resin.

The film can be obtained by subjecting any of the variety of resins as the film-forming material to extrusion or other processes. Printing may also be performed in various ways on the film.

The film may also contain an additive such as the organic ultraviolet-absorbing agent (a), the powdery inorganic ultraviolet blocking agent (b), a weather resistance improver, a light stabilizer, a filler, a pigment, a flame retardant, an antibacterial agent, an antifungal agent, or an anti-blocking agent.

Examples of the synthetic resin used to form the synthetic resin container include polyethylene, polyamide, polyester, polyvinyl alcohol, ethylene-vinyl alcohol copolymers, fluororesin, and silicone resin.

The synthetic resin may also be mixed with an additive such as the organic ultraviolet-absorbing agent (a), the powdery inorganic ultraviolet blocking agent (b), a light stabilizer, a preservative, a flame retarder, or an antioxidant.

The synthetic resin container can be obtained by performing injection molding, blow molding, or other type molding of a synthetic resin composition containing the benzylidene hydantoin derivative or the salt according to the invention and optionally the additive. Printing may also be performed in various ways on the resulting synthetic resin container.

Examples of the material used to form the contact lens include siloxane-containing polymers, silicone-(meth)acrylate resin, and silicone-styrene resin. The contact lens may also contain an additive such as the organic ultraviolet-absorbing agent (a), the powdery inorganic ultraviolet blocking agent (b), an alcohol, or a colorant.

Examples of the resin or polymer used to form the fibers include polyamide, polyphenylene sulfide, polyester, cellulose, polyurethane, and polyether.

The fibers may also contain the an organic ultraviolet-absorbing agent other than the aminophenol derivative or the salt thereof according to the invention, a pigment, an antioxidant, a heat resistant stabilizer, a plasticizer, a flame retardant, or a conductivity imparting agent.

The ultraviolet-absorbing agent according to the invention may also be subjected to chemical modification such as microencapsulation and then used as various process materials.

[Method for Producing Benzylidene Azolidine Derivative and Salt Thereof]

For example, as shown in reaction formula (1), a compound (a) of formula (a) below is allowed to react with a compound (b) of formula (b) below in the presence of a base to form a compound (c) of formula (c) below. As shown in reaction formula (2), the compound of formula (c) is then allowed to react with a compound (d) of formula (d) below in the presence of a base to form a benzylidene azolidine derivative according to the invention.

[Formula 14]

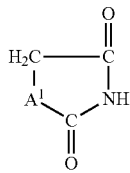
(a)

$A^1$ in formula (a) has the same meaning as $A^1$ in formula (I).

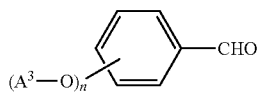
(b)

$A^3$ in formula (b) has the same meaning as $A^3$ in formula (I).

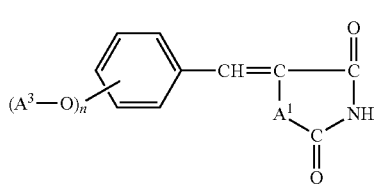
(c)

$A^1$ and $A^3$ in formula (a) have the same meaning as $A^1$ and $A^3$ in formula (I), respectively.

Y-$A^2$ (d)

In formula (d), Y represents a halogen atom such as chlorine, bromine, or iodine or a sulfonate group represented by —OSO$_2$R', wherein R' represents a methyl group, a p-tolyl group, a trifluoromethyl group, a pentafluoroethyl group, or a nonafluorobutyl group, and $A^2$ in formula (d) has the same meaning as $A^2$ in formula (I).

Reaction formula (1)

[Formula 15]

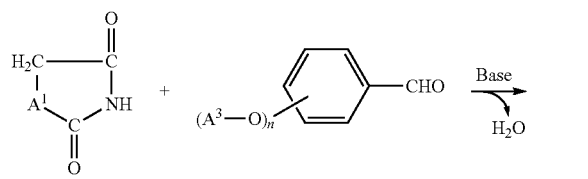

Reaction formula (2)

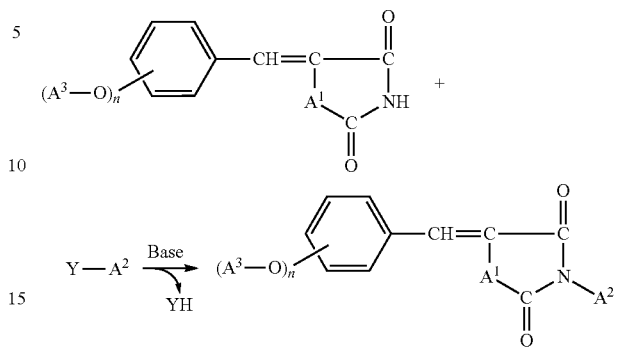

In this reaction, a commercially available product may be used directly as the compound (b). The compound (b) to be used, which has a functional group other than a hydrogen atom for $A^3$, may also be obtained, as shown in reaction formula (3), by allowing a compound (b') of structural formula (b') below having a hydrogen atom for $A^3$ to react with a compound (e) of structural formula (e) below in the presence of a base.

[Formula 16]

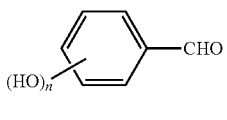
(b')

Y—$A^3$ (e)

$A^3$ in formula (e) has the same meaning as $A^1$ in formula (I), exclusive of a hydrogen atom.

Reaction formula (3)

[Formula 17]

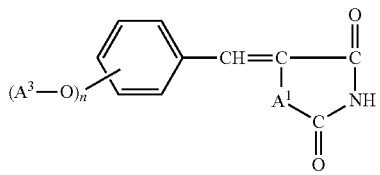

A commercially available product may also be used directly as the compound (a).

As shown in reaction formula (5) below, the compound (a) may be allowed to react with the compound (d) in the presence of a base to form a compound (f) of formula (f) below. When $A^1$ is NH in the compound (a), as shown in reaction formula (5'), the compound (f) may be allowed to react with a compound of structural formula (e') below in the presence of a base so that the compound (f) is substituted with $A^4$ at the $A^1$ position. As shown in reaction formula (6) below, the compound (f) may be then allowed to react with the compound (b) in the presence of a base so that the benzylidene azolidine derivative according to the invention can also be synthesized.

[Formula 18]

Reaction formula (5)

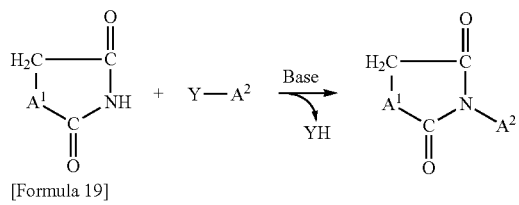

[Formula 19]

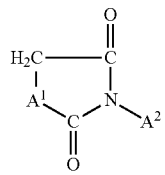
(f)

A¹ and A² in formula (f) have the same meaning as A¹ and A² in formula (I), respectively.

[Formula 20]

Y-A⁴  (e')

A⁴ in formula (e') has the same meaning as A⁴ in formula (I), exclusive of a hydrogen atom.

[Formula 21]

Reaction formula (5')

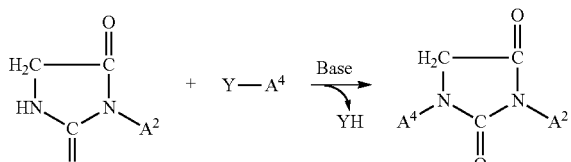

[Formula 22]

Reaction formula (6)

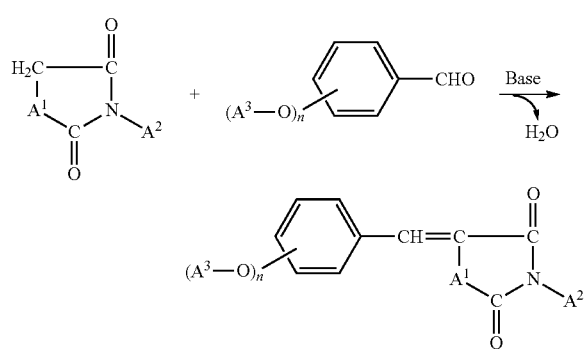

When the benzylidene azolidine derivative according to the invention has the functional group (2) or (3) for $A^2$, $A^3$, and $A^4$ in structural formula (I), a compound (h) having a functional group (h) of structural formula (h) below may be synthesized using the same process as shown in reaction formulae (1) to (6), except that a compound (g) of structural formula (g) below is used instead of the compound (d), (e), or (e'), and then the compound (h) may be subjected to a common functional group conversion reaction (such as esterification of carboxylic acid, amidation of carboxylic acid, transesterification, or amidation of ester), so that the benzylidene azolidine derivative according to the invention can also be obtained.

[Formula 23]

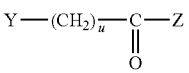
(g)

In formula (g), Y has the same meaning as Y in formula (d), u is 1 or 2, and Z is a hydroxyl group or an alkoxyl group.

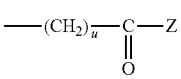
(h)

In formula (h), u is 1 or 2, and Z is a hydroxyl group or an alkoxyl group.

As described above, a base is used in the process of producing the benzylidene azolidine derivative according to the invention. Such a base may be, for example, sodium carbonate, potassium carbonate, sodium hydride, pyrrolidine, piperidine, sodium acetate, or ammonia water.

The salt of the benzylidene azolidine derivative according to the invention can be produced by a process including adding an inorganic acid such as hydrochloric acid, sulfuric acid, nitric acid, phosphoric acid, or hydrobromic acid, or an organic acid such as acetic acid, citric acid, gluconic acid, tartaric acid, fumaric acid, maleic acid, lactic acid, methanesulfonic acid, or p-toluenesulfonic acid to the benzylidene azolidine derivative obtained as described above to neutralize it, removing the solvent by distillation, and purifying the product.

EXAMPLES

Hereinafter, the invention will be described with reference to examples, which, however, are not intended to limit the invention.

Example 1

(1) Production of Compound 1

In a 300 mL egg-plant shaped flask, 14.7 g (120 mmol) of 4-hydroxybenzaldehyde was mixed with 16.4 g (132 mmol) of 2-(2-chloroethoxyl)ethanol, 33.2 g (240 mmol) of potassium carbonate, and 150 mL of acetonitrile. The mixture was heated at 105° C. for 14 hours with stirring. Thereafter, 1.49 g (12.0 mmol) of 2-(2-chloroethoxy) ethanol was further added, and the mixture was heated at 105° C. for 30 hours with stirring. After the liquid reaction mixture was cooled to room temperature, the solid was removed by celite filtration. The solvent was removed by distillation under reduced pressure, so that 34.6 g of a yellow viscous material mixed with a white solid was obtained. To the product was added 80 mL of water. The mixture was transferred into a separate 200 mL egg-plant shaped flask, and 15.6 g (156 mmol) of hydantoin and 14.4 g of 28% ammonia water were added to the flask. The mixture was heated at 90° C. for 12 hours with stirring. After the liquid reaction mixture was cooled to room temperature, the precipitated crystals were collected by filtration. The crystals were then washed twice with water and twice with ethanol. The crystals were dried to give 29.6 g of 5-[4-[2-(2-hydroxyethoxy)ethoxy]benzylidene]hydantoin. Subsequently, 17.5 g (60.0 mmol) of the product was added to a 200 mL egg-plant shaped flask, and 7.47 g (60 mmol) of 2-(2-chloroethoxyl)ethanol, 20.0 g (145 mmol) of potassium carbonate, and 80 mL of N,N-dimethylformamide were added to the flask. The mixture was heated at 110° C. for 3 hours with stirring. After the liquid reaction mixture was cooled to room temperature, the solid was removed by celite filtration. The solvent was removed by distillation under reduced pressure, so that 30.5 g of a yellow viscous material mixed with a white solid was obtained. The product was purified by silica gel column chromatography (developing solvent: isopropanol/toluene=1/3) to give 9.21 g of yellow crystals. The product was subjected to an activated carbon treatment with ethanol to give 6.56 g of compound 1 (yield: 25%).

<Evaluation of Hydrophilicity>

When the resulting compound 1 was dissolved in the test solvent shown below, the behavior was observed and the solubility (g/100 g test solvent) of the compound 1 in 100 g of the test solvent at 25° C. was determined.

Test solvent: A mixed solvent containing 10% by weight of dipropylene glycol, 10% by weight of ethanol, and 80% by weight of purified water (based on 100% by weight of the total amount of dipropylene glycol, ethanol, and purified water).

[Formula 24]

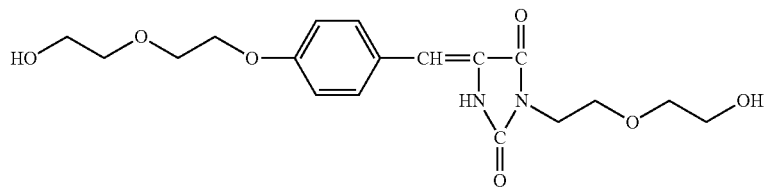

5-[4-[2-(2-hydroxyethoxyl)ethoxy]benzylidene]-3-[2-(2-hydroxyethoxyl)ethyl]hydantoin The above structural formula of the resulting compound 1 was determined from the $^1$H-NMR spectrum under the following measurement conditions.

<Measurement Conditions>

Analyzer: Proton nuclear magnetic resonance spectrometer (JNM-ECP500 manufactured by JEOL Ltd.)

Internal standard: Tetramethylsilane

Solvent: DMSO-d6 (hexadeuterodimethyl sulfoxide)

Important chemical shift peaks of compound 1 for DMSO-d6 (standard substance) are as follows.

3.41-3.46 (m, 4H), 3.48-3.53 (m, 4H), 3.60 (m, 2H), 3.64 (m, 2H), 3.75 (t, 2H), 4.15 (t, 2H), 4.61 (t, 1H), 4.67 (t, 1H), 6.52 (s, 1H), 6.99 (d, 2H), 7.62 (d, 2H), 10.71 (s, 1H)

(2) Evaluation of the Properties of Compound 1

<UV Absorbing Properties>

The resulting compound 1 was dissolved at a concentration of 5 ppm in ethanol as a solvent to form a sample solution. After the prepared sample solution was injected into a quartz cell (1 cm in optical path length), the UV spectrum of the sample was measured with a spectrophotometer (UV-2450 manufactured by SHIMADZU CORPORATION), in which the maximal absorption wavelength (λmax) and the absorbance at the maximal absorption wavelength were determined. When the maximal absorption wavelength falls within the ultraviolet wavelength range, the higher absorbance at the maximal absorption wavelength indicates the better UV absorbing properties. Table 1 shows the results.

Based on the difference in solubility, the hydrophilicity was evaluated as follows.

Particularly high hydrophilicity: A solubility of 1.0 or more (g/100 g test solvent)

High hydrophilicity: A solubility of 0.2 to less than 1.0 (g/100 g test solvent)

Low hydrophilicity: A solubility of 0.1 to less than 0.2 (g/100 g test solvent)

No hydrophilicity: A solubility of less than 0.1 (g/100 g test solvent) or the occurrence of suspended solids Example 2

First, 27.2 g of 5-[4-[2-[2-(2-hydroxyethoxyl)ethoxy]ethoxy]benzylidene]hydantoin was obtained as in Example 1, except that 2-[2-(2-chloroethoxyl)ethoxy]ethanol was used instead of 2-(2-chloroethoxyl)ethanol. Subsequently, 2.24 g (6.67 mmol) of the product was added to a 100 mL egg-plant shaped flask, and 2.53 g (15.0 mmol) of 2-[2-(2-chloroethoxyl)ethoxy]ethanol, 2.07 g (15.0 mmol) of potassium carbonate, and 30 mL of N,N-dimethylformamide were added to the flask. The mixture was heated at 110° C. for 15 hours with stirring. After the liquid reaction mixture was cooled to room temperature, the solid was removed by celite filtration. The solvent was removed by distillation under reduced pressure, so that 6.53 g of a yellow viscous material mixed with a white solid was obtained. The product was purified by silica gel column chromatography (developing solvent: chloroform/methanol=20/1) to give 1.08 g of compound 2 (yellow oil, yield 35%).

The $^1$H-NMR spectrum chart of compound 2 was obtained as in Example 1. The resulting spectrum chart showed that compound 2 has the following structure.

[Formula 25]

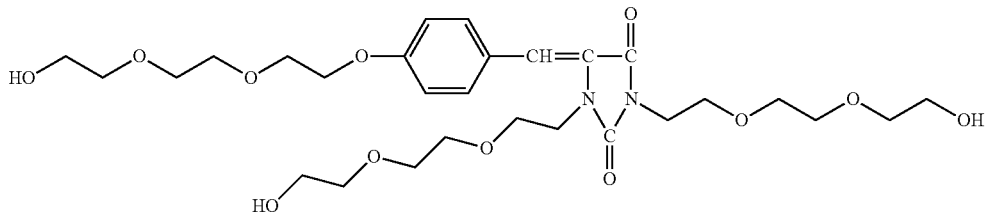

5-[4-[2-[2-(2-hydroxyethoxyl)ethoxy]ethoxy]benzylidene]-1,3-bis[2-[2-(2-hydroxyethoxyl)ethoxy]ethyl]hydantoin Important chemical shift peaks of compound 2 for DMSO-d6 (standard substance) are as follows.

3.06 (t, 2H), 3.25 (t, 2H), 3.31-3.34 (m, 4H), 3.39-3.43 (m, 8H), 3.48-3.55 (m, 8H), 3.59-3.61 (m, 4H), 3.67 (t, 2H), 3.71-3.76 (m, 4H), 4.13 (t, 2H), 4.59 (br, 1H×3), 6.80 (s, 1H), 7.00 (d, 2H), 7.37 (d, 2H)

The UV absorbing properties and the hydrophilicity of compound 2 were then evaluated as in Example 1. Table 1 shows the results.

Example 3

In a 200 mL egg-plant shaped flask, 14.7 g (120 mmol) of 4-hydroxybenzaldehyde was mixed with 15.6 g (156 mmol) of hydantoin, 80 mL of water, and 14.4 g of 28% ammonia water, and the mixture was heated at 90° C. for 12 hours with stirring. After the liquid reaction mixture was cooled to room temperature, the precipitated crystals were collected by filtration. The crystals were then washed twice with water and twice with ethanol. The crystals were dried to give 20.3 g of 5-(4-hydroxybenzylidene)hydantoin. Subsequently, 18.8 g (92.2 mmol) of the product was added to a 500 mL egg-plant shaped flask and then dissolved in 180 mL of N,N-dimethylformamide. To the solution were added to 27.1 g (221 mmol) of ethyl chloroacetate and 30.5 g (221 mmol) of potassium carbonate. The mixture was heated at 120° C. for 2 hours with stirring. After the liquid reaction mixture was cooled to room temperature, the solvent was removed by distillation under reduced pressure. Water was added to the residue, and then the mixture was extracted three times with ethyl acetate. The organic layers were collected, washed twice with water and once with saturated brine, and then dried with sodium sulfate. The sodium sulfate was then removed by filtration. After the solvent was removed by distillation under reduced pressure, the resulting brown crystals were recrystallized with a mixed solvent of ethyl acetate and hexane. The crystals were then dried to give 9.96 g of 5-[4-(2-ethoxy-2-oxoethoxy)benzylidene]-3-(2-ethoxy-2-oxoethyl)hydantoin. In a 50 mL egg-plant shaped flask, 4.50 g (12.0 mmol) of the product was mixed with 7.57 g (72.0 mmol) of diethanolamine, and the mixture was heated at 120° C. for 1 hour with stirring. After the liquid reaction mixture was cooled to room temperature, the precipitated yellow crystals were recrystallized with a mixed solvent of ethanol and water. The crystals were then dried to give 4.46 g of compound 3 (yield: 18%).

The ¹H-NMR spectrum chart of compound 3 was obtained as in Example 1. The resulting spectrum chart showed that compound 3 has the following structure.

[Formula 26]

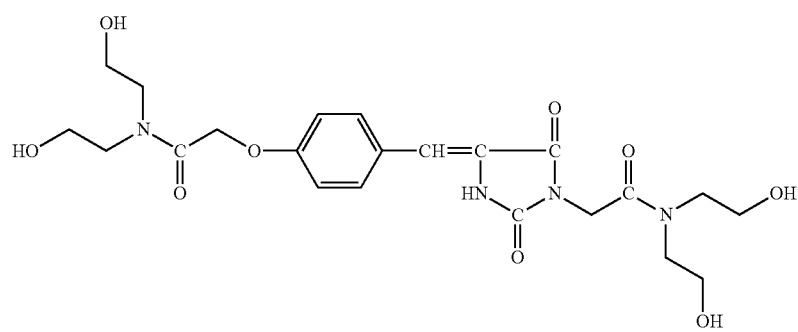

5-[4-[2-[bis(2-hydroxyethyl)amino]-2-oxoethoxy]benzylidene]-3-[2-[bis(2-hydroxyethyl)amino]-2-oxoethyl]hydantoin Important chemical shift peaks of compound 3 for DMSO-d6 (standard substance) are as follows.

3.33-3.36 (m, 4H), 3.42-3.51 (m, 8H), 3.57-3.60 (m, 4H), 4.49 (s, 2H), 4.71-4.74 (t, 1H×2), 4.97 (s, 2H), 5.00 (t, 1H), 5.05 (t, 1H), 6.53 (s, 1H), 6.94 (d, 2H), 7.60 (d, 2H), 10.72 (s, 1H)

The UV absorbing properties and the hydrophilicity of compound 3 were then evaluated as in Example 1. Table 1 shows the results.

Example 4

In 200 mL egg-plant shaped flask, 5.84 g (20.0 mmol) of 5-[4-[2-(2-hydroxyethoxy)ethoxy]benzylidene]hydantoin obtained in the process of Example 1 was mixed with 2.40 g (24.0 mmol) of ethyl acrylate, 0.112 g (2.00 mmol) of potassium hydroxide, and 45 mL of N,N-dimethylformamide, and the mixture was heated at 110° C. for 6 hours with stirring. After the liquid reaction mixture was cooled to room temperature, the solid was removed by celite filtration. The solvent was removed by distillation under reduced pressure, so that a yellow viscous material was obtained. In a separate 100 mL egg-plant shaped flask, the product was mixed with 6.31 g (60.0 mmol) of diethanolamine, and the mixture was heated at 120° C. for 17 hours with stirring. After the liquid reaction mixture was cooled to room temperature, acetonitrile and isopropanol were added to the resulting orange viscous material, so that crystals were precipitated. The precipitated crystals were collected by filtration. The crystals were subjected to an activated carbon treatment with isopropanol and water and recrystallized to give 3.52 g of compound 4 (yield: 39%).

The ¹H-NMR spectrum chart of compound 4 was obtained as in Example 1. The resulting spectrum chart showed that compound 4 has the following structure.

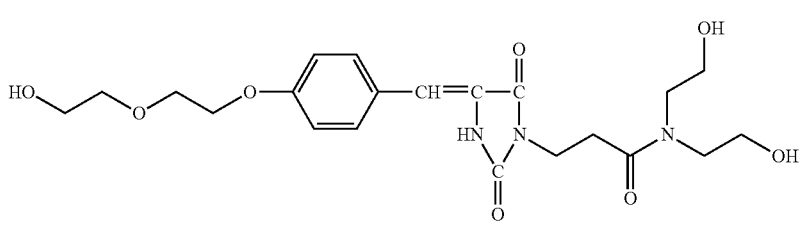

[Formula 27]

5-[4-[2-(2-hydroxyethoxyl)ethoxy]benzylidene]-3-[3-[bis(2-hydroxyethyl)amino]-3-oxopropyl]hydantoin Important chemical shift peaks of compound 4 for DMSO-d6 (standard substance) are as follows.

2.72 (t, 2H), 3.32-3.38 (m, 4H), 3.46-3.52 (m, 8H), 3.66 (t, 2H), 3.75 (t, 2H), 4.14 (t, 2H), 4.69 (s, 2H), 4.85 (s, 1H), 6.47 (s, 1H), 6.98 (d, 2H), 7.62 (d, 2H), 10.60 (s, 1H)

The UV absorbing properties and the hydrophilicity of compound 4 were then evaluated as in Example 1. Table 1 shows the results.

Example 5

Compound 5 was obtained as in Example 3, except that diethylene glycol was used instead of diethanolamine.

The $^1$H-NMR spectrum chart of compound 5 was obtained as in Example 1. The resulting spectrum chart showed that compound 5 has the following structure.

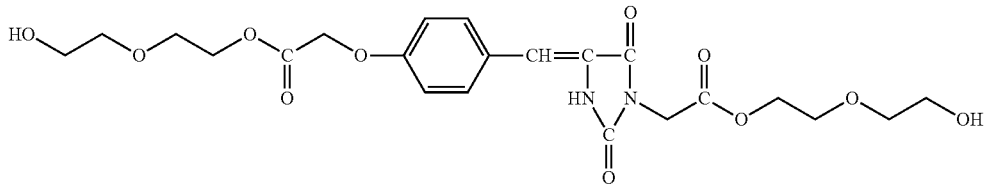

[Formula 28]

5-[4-[2-[2-(2-hydroxyethoxyl)ethoxy]-2-oxoethoxy]benzylidene]-3-[2-[2-(2-hydroxyethoxyl)ethoxy]-2-oxoethyl]hydantoin Important chemical shift peaks of compound 5 for DMSO-d6 (standard substance) are as follows.

3.43-3.45 (m, 4H), 3.48-3.51 (m, 4H), 3.63-3.66 (m, 4H), 4.23-4.27 (m, 4H), 4.34 (s, 2H), 4.89 (s, 2H), 4.62-4.65 (t, 1H×2), 6.60 (s, 1H), 6.99 (d, 2H), 7.64 (d, 2H), 10.91 (s, 1H)

The UV absorbing properties and the hydrophilicity of compound 5 were then evaluated as in Example 1. Table 1 shows the results.

Example 6

First, 24.6 g of 5-(4-methoxybenzylidene]hydantoin was obtained as in Example 1, except that 4-methoxybenzaldehyde was used instead of 4-hydroxybenzaldehyde. In a 300 mL egg-plant shaped flask, 24.4 g (112 mmol) of the resulting 5-(4-methoxybenzylidene]hydantoin was then dissolved in 110 mL of N,N-dimethylformamide. Subsequently, 28.8 g (235 mmol) of ethyl chloroacetate and 32.5 g (235 mmol) of potassium carbonate were added to the flask. The mixture was heated at 120° C. for 30 minutes with stirring. After the liquid reaction mixture was cooled to room temperature, the solvent was removed by distillation under reduced pressure. Water was added to the residue, and the mixture was extracted three times with ethyl acetate. The organic layers were collected, washed twice with water and once with saturated brine, and then dried with sodium sulfate. The sodium sulfate was then removed by filtration. The solvent was removed by distillation under reduced pressure, so that 48.6 g of a yellow oil was obtained, 24.3 g of which was added to a separate 200 mL egg-plant shaped flask and then mixed with 47.1 g (448 mmol) of diethanolamine. The mixture was heated at 120° C. for 6 hours with stirring. After the liquid reaction mixture was cooled to room temperature, the resulting orange viscous material was purified by silica gel column chromatography (developing solvent: chloroform/methanol=5/1) to give 6.75 g of compound 6 (yellow oil, yield 22%).

The $^1$H-NMR spectrum chart of compound 6 was obtained as in Example 1. The resulting spectrum chart showed that compound 6 has the following structure.

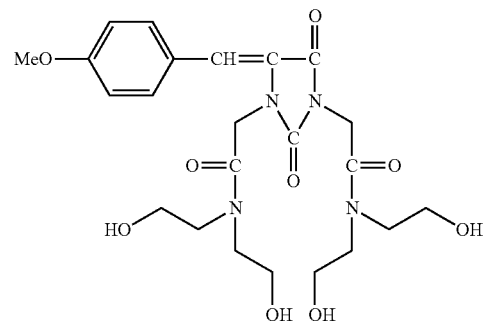

[Formula 29]

5-(4-methoxybenzylidene]-1,3-bis[2-[bis(2-hydroxyethyl)amino]-2-oxoethyl]hydantoin Important chemical shift peaks of compound 6 for DMSO-d6 (standard substance) are as follows.

3.33-3.36 (m, 4H), 3.45-3.51 (m, 6H), 3.54-3.66 (m, 6H), 3.79 (s, 3H), 4.53 (s, 2H), 4.73 (t, 2H), 4.75 (s, 2H), 4.99 (t, 1H), 5.24 (t, 1H), 6.37 (s, 1H), 6.95 (d, 2H), 7.95 (d, 2H)

The UV absorbing properties and the hydrophilicity of compound 6 were then evaluated as in Example 1. Table 1 shows the results.

Example 7

Compound 7 was obtained as in Example 6, except that diethylene glycol was used instead of diethanolamine.

The $^1$H-NMR spectrum chart of compound 7 was obtained as in Example 1. The resulting spectrum chart showed that compound 7 has the following structure.

[Formula 30]

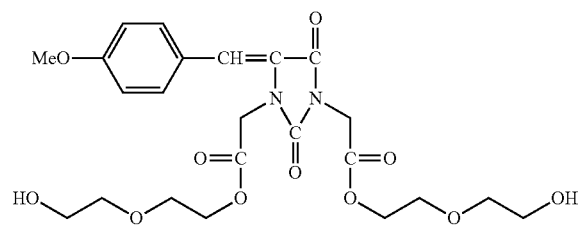

5-(4-methoxybenzylidene)-1,3-bis[2-[2-(2-hydroxy-ethoxy)ethoxy]-2-oxoethyl]hydantoin Important chemical shift peaks of compound 7 for DMSO-d6 (standard substance) are as follows.

3.40-3.47 (m, 8H), 3.50 (t, 2H), 3.64 (t, 2H), 3.80 (s, 3H), 3.98 (t, 2H), 4.25 (t, 2H), 4.33 (s, 2H), 4.43 (s, 2H), 4.59 (t, 1H), 4.64 (t, 1H), 6.90 (s, 1H), 6.99 (d, 2H), 7.30 (d, 2H)

The UV absorbing properties and the hydrophilicity of compound 7 were then evaluated as in Example 1. Table 1 shows the results.

Comparative Example 1

Using 2-ethylhexyl dimethoxybenzylidene dioxoimidazolidine propionate (Soft Shade DH (registered trademark) manufactured by Ajinomoto Co., Inc.) instead of compound 1, the UV absorbing properties of the compound were evaluated as in Example 1. Its hydrophilicity was also evaluated as in Example 1. Table 1 shows the results. Hereinafter, 2-ethylhexyl dimethoxybenzylidene dioxoimidazolidine propionate is called "compound 1'."

[Formula 31]

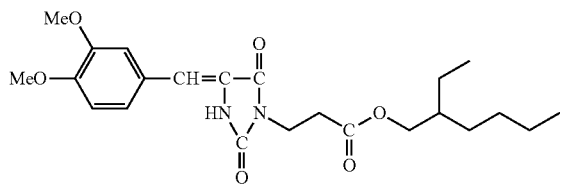

TABLE 1

| Test Examples | Compound name | Maximal absorption wavelength (λmax) (in units of nm) | Absorbance at maximal absorption wavelength | Solubility* (g/100 g test solvent) |
|---|---|---|---|---|
| Example 1 | Compound 1 | 335 | 0.43 | 2.0 |
| Example 2 | Compound 2 | 325 | 0.12 | 25< |
| Example 3 | Compound 3 | 336 | 0.30 | 1.2 |
| Example 4 | Compound 4 | 338 | 0.34 | 1.5 |
| Example 5 | Compound 5 | 335 | 0.20 | 0.2 |
| Example 6 | Compound 6 | 328 | 0.18 | 25< |
| Example 7 | Compound 7 | 326 | 0.14 | 25< |
| Comparative Example 1 | Compound 1' | 347 | 0.30 | <0.05 |

*Compounds 1 to 7 and compound 1' were each added to the test solvent. In this process, compounds 1 to 7 were each uniformly dissolved in the test solvent. The resulting solution containing each of these compounds was clear (each compound had particularly high or high hydrophilicity). In contrast, compound 1' was suspended in the test solvent without being dissolved (it had no hydrophilicity).

The invention claimed is:

1. A benzylidene azolidine derivative represented by structural formula (I) or salt thereof:

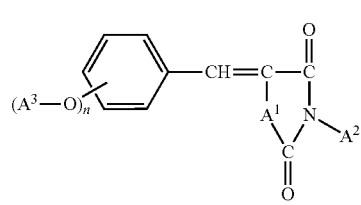

(I)

wherein n is an integer of 1 to 5, $A^1$ is O, S, or N-$A^4$, $A^2$, $A^3$, and $A^4$ are each independently a hydrogen atom, an optionally hydroxyl-substituted alkyl group of 1 to 8 carbon atoms, a functional group (1) represented by structural formula (1):

(1)

wherein $X^1$ is an alkylene group of 2 to 4 carbon atoms, $R^1$ is a hydroxyalkyl group of 2 to 4 carbon atoms, and m is an integer of 1 to 4, provided that when m is an integer of 2 to 4, two or more occurrences of $X^1$ may be the same or different, a functional group (2) represented by structural formula (2):

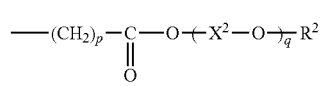

(2)

wherein $X^2$ is an alkylene group of 2 to 4 carbon atoms, $R^2$ is a hydroxyalkyl group of 2 to 4 carbon atoms, p is 1 or 2, and q is an integer of 0 to 4, provided that when q is an integer of 2 to 4, two or more occurrences of $X^2$ may be the same or different, or a functional group (3) represented by structural formula (3):

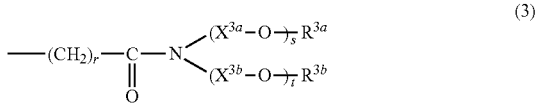

wherein $X^{3a}$ and $X^{3b}$ are each independently an alkylene group of 2 to 4 carbon atoms, $R^{3a}$ and $R^{3b}$ are each independently a hydroxyalkyl group of 2 to 4 carbon atoms, r is 1 or 2, s and t are each independently an integer of 0 to 4, provided that when s is an integer of 2 to 4, two or more occurrences of $X^{3a}$ may be the same or different and when t is an integer of 2 to 4, two or more occurrences of $X^{3b}$ may be the same or different, provided that at least one of $A^2$, $A^3$, and $A^4$ has at least one hydroxyl group and provided that when n is an integer of 2 to 5, two or more occurrences of $A^3O$— may be the same or different, or a salt thereof, and at least one of $A^2$, $A^3$, and $A^4$ in structural formula (I) is the functional group (1), (2), or (3).

2. The benzylidene azolidine derivative or salt thereof according to claim 1, which is a benzylidene derivative represented by structural formula (II):

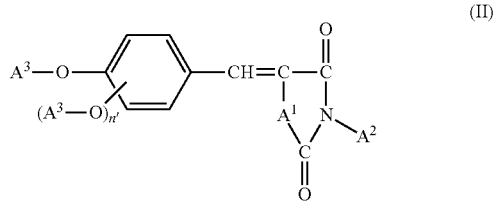

wherein n' is an integer of 0 to 4, provided that when n' is an integer of 1 to 4, two or more occurrences of $A^3$-O— may be the same or different, or a salt thereof.

3. The benzylidene azolidine derivative or salt thereof according to claim 1, which is a benzylidene hydantoin derivative represented by structural formula (III):

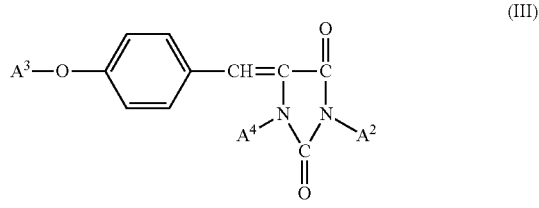

or a salt thereof.

4. A composition for external use on skin, comprising a benzylidene azolidine derivative represented by structural formula (I) or salt thereof:

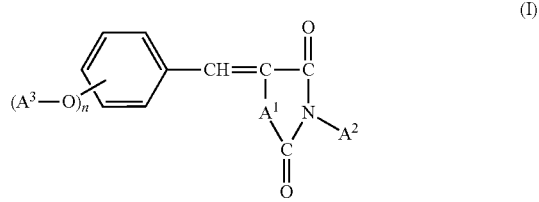

wherein n is an integer of 1 to 5, $A^1$ is O, S, or N-$A^4$, $A^2$, $A^3$, and $A^4$ are each independently a hydrogen atom, an optionally hydroxyl-substituted alkyl group of 1 to 8 carbon atoms, a functional group (1) represented by structural formula (1):

wherein $X^1$ is an alkylene group of 2 to 4 carbon atoms, $R^1$ is a hydroxyalkyl group of 2 to 4 carbon atoms, and m is an integer of 1 to 4, provided that when m is an integer of 2 to 4, two or more occurrences of $X^1$ may be the same or different, a functional group (2) represented by structural formula (2):

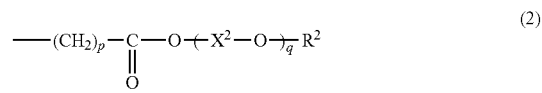

wherein $X^2$ is an alkylene group of 2 to 4 carbon atoms, $R^2$ is a hydroxyalkyl group of 2 to 4 carbon atoms, p is 1 or 2, and q is an integer of 0 to 4, provided that when q is an integer of 2 to 4, two or more occurrences of $X^2$ may be the same or different, or a functional group (3) represented by structural formula (3):

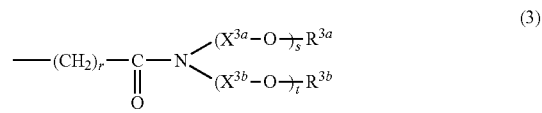

wherein $X^{3a}$ and $X^{3b}$ are each independently an alkylene group of 2 to 4 carbon atoms, $R^{3a}$ and $R^{3b}$ are each independently a hydroxyalkyl group of 2 to 4 carbon atoms, r is 1 or 2, s and t are each independently an integer of 0 to 4, provided that when s is an integer of 2 to 4, two or more occurrences of $X^{3a}$ may be the same or different and when t is an integer of 2 to 4, two or more occurrences of $X^{3b}$ may be the same or different, provided that at least one of $A^2$, $A^3$, and $A^4$ has at least one hydroxyl group and provided that when n is an integer of 2 to 5, two or more occurrences of $A^3O$— may be the same or different, or a salt thereof, and at least one of $A^2$, $A^3$, and $A^4$ in structural formula (I) is the functional group (1), (2), or (3).

5. A composition for external use to skin according to claim 4, wherein at least one of $A^2$ and $A^3$ in structural formula (I) is a hydrogen atom, a hydroxyl-substituted alkyl group of 1 to 8 carbon atoms, or the functional group (1), (2), or (3).

6. A composition for external use to skin according to claim 4, which is the benzylidene azolidine derivative represented by structural formula (II):

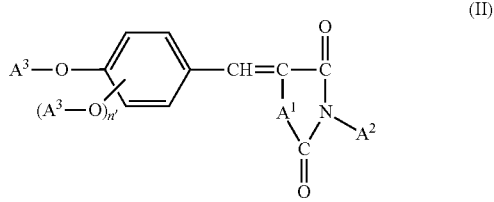

wherein n' is an integer of 0 to 4, provided that when n' is an integer of 1 to 4, two or more occurrences of $A^3$-O— may be the same or different, or a salt thereof.

7. A composition for external use to skin according to claim 4, wherein the benzylidene azolidine derivative is a benzylidene hydantoin derivative represented by structural formula (III):

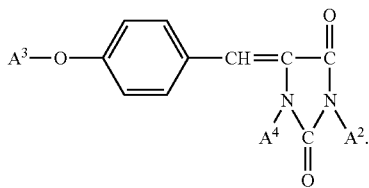
(III)

8. A method of absorbing an ultraviolet ray comprising applying to a subject a benzylidene azolidine derivative represented by structural formula (I) or salt thereof:

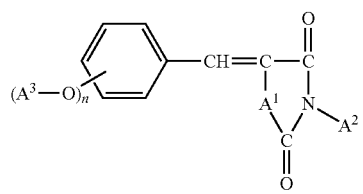
(I)

wherein n is an integer of 1 to 5, $A^1$ is O, S, or N-$A^4$, $A^2$, $A^3$, and $A^4$ are each independently a hydrogen atom, an optionally hydroxyl-substituted alkyl group of 1 to 8 carbon atoms, a functional group (1) represented by structural formula (1):

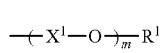
(1)

wherein $X^1$ is an alkylene group of 2 to 4 carbon atoms, $R^1$ is a hydroxyalkyl group of 2 to 4 carbon atoms, and m is an integer of 1 to 4, provided that when m is an integer of 2 to 4, two or more occurrences of $X^1$ may be the same or different, a functional group (2) represented by structural formula (2):

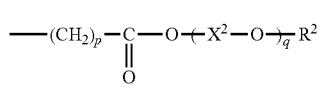
(2)

wherein $X^2$ is an alkylene group of 2 to 4 carbon atoms, $R^2$ is a hydroxyalkyl group of 2 to 4 carbon atoms, p is 1 or 2, and q is an integer of 0 to 4, provided that when q is an integer of 2 to 4, two or more occurrences of $X^2$ may be the same or different, or a functional group (3) represented by structural formula (3):

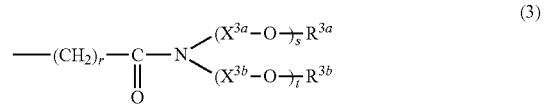
(3)

wherein $X^{3a}$ and $X^{3b}$ are each independently an alkylene group of 2 to 4 carbon atoms, $R^{3a}$ and $R^{3b}$ are each independently a hydroxyalkyl group of 2 to 4 carbon atoms, r is 1 or 2, s and t are each independently an integer of 0 to 4, provided that when s is an integer of 2 to 4, two or more occurrences of $X^{3a}$ may be the same or different and when t is an integer of 2 to 4, two or more occurrences of $X^{3b}$ may be the same or different, provided that at least one of $A^2$, $A^3$, and $A^4$ has at least one hydroxyl group and provided that when n is an integer of 2 to 5, two or more occurrences of $A^3$O— may be the same or different, or a salt thereof, wherein at least one of $A^2$, $A^3$, and $A^4$ in structural formula (I) is the functional group (1), (2), or (3).

9. The method of absorbing the ultraviolet ray according to claim 8, wherein at least one of $A^2$ and $A^3$ in structural formula (I) is a hydrogen atom, a hydroxyl-substituted alkyl group of 1 to 8 carbon atoms, or the functional group (1), (2), or (3).

10. The method of absorbing the ultraviolet ray according to claim 8, which is the benzylidene azolidine derivative represented by structural formula (II):

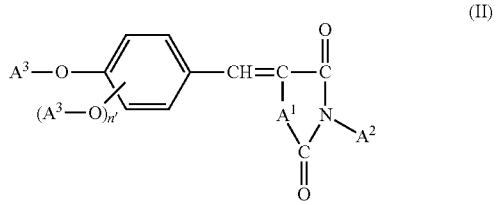
(II)

wherein n' is an integer of 0 to 4, provided that when n' is an integer of 1 to 4, two or more occurrences of $A^3$-O— may be the same or different, or a salt thereof.

11. The method of absorbing the ultraviolet according to claim 8, wherein the benzylidene azolidine derivative is a benzylidene hydantoin derivative represented by structural formula (III):

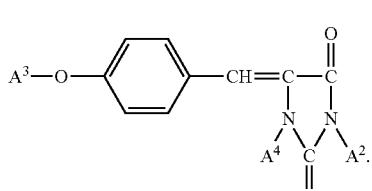
(III)

* * * * *